United States Patent [19]

Augstein et al.

[11] 4,085,115
[45] Apr. 18, 1978

[54] CARBOXAMIDO TETRAZOLES

[75] Inventors: Joachim Augstein; Hugh Cairns; Norman Harold Rogers, all of Loughborough, England

[73] Assignee: Fisons Limited, England

[21] Appl. No.: 674,732

[22] Filed: Apr. 6, 1976

Related U.S. Application Data

[63] Continuation of Ser. No. 421,282, Dec. 3, 1973, abandoned.

[30] Foreign Application Priority Data

Dec. 5, 1972 United Kingdom .............. 55997/72
Aug. 13, 1973 United Kingdom .............. 39046/73

[51] Int. Cl.² .................. C07D 257/04; A61K 31/41; C07D 493/04
[52] U.S. Cl. ................................ 260/308 D; 424/269
[58] Field of Search .................... 421/282; 260/308 D

[56] References Cited

U.S. PATENT DOCUMENTS 3,879,411 4/1975 Cairns et al. .................... 260/308 D
3,887,574 6/1975 Ellis et al. ........................ 260/308 D Primary Examiner—Frederick E. Waddell
Attorney, Agent, or Firm—Wenderoth, Lind & Ponack

[57] ABSTRACT

There are described compounds of formula Ix,

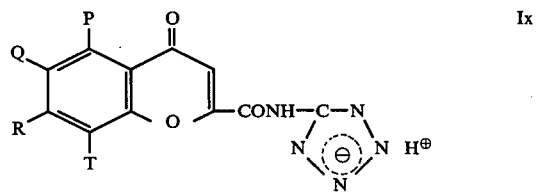

in which one or more adjacent pairs of P, Q, R and T represent a chain of formula XX,

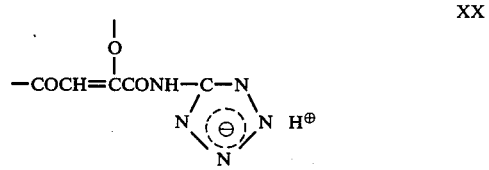

or a group of formula X,

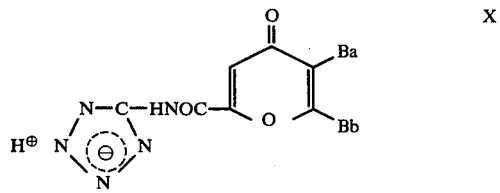

in which Ba and Bb represent the pair of groups:- a carbon-carbon bond and —CRa=CRb—; or an adjacent pair of P, Q, R and T represent a group of formula XI,

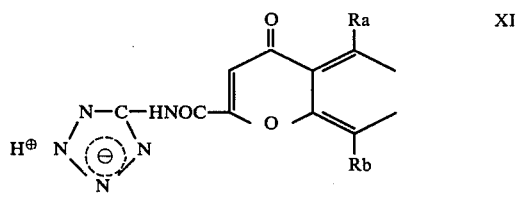

Ra and Rb and those of P, Q, R and T which do not form a chain of formula XX or a group of formula X or XI may be the same or different and each represents hydrogen; alkyl; alkoxy; alkenyl; alkenyloxy; alkyl or alkoxy, substituted by a hydroxy, alkoxy, aryl or halo group; amino; mono- or di-lower alkylamino; aminoalkoxy; aminoalkoxy substituted by a lower alkyl group; nitro; hydroxy; halogen; acyl; or aryloxy.

There are also described processes for making the compounds and pharmaceutical, e.g. anti-allergic, compositions containing them.

3 Claims, No Drawings

CARBOXAMIDO TETRAZOLES

This is a continuation, of application Ser. No. 421,282, filed Dec. 3, 1973, now abandoned.

This invention relates to new benzo- and naphtho-dipyran derivatives.

According to our invention we provide a compound (to be called a compound I) in which two chains of formula XX,

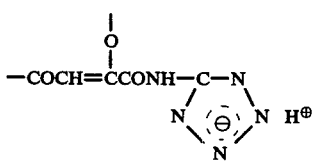

XX are attached respectively to two pairs of ortho positions on a benzene or naphthalene nucleus, and pharmaceutically acceptable derivatives thereof. More specifically we provide compounds of formula Ix,

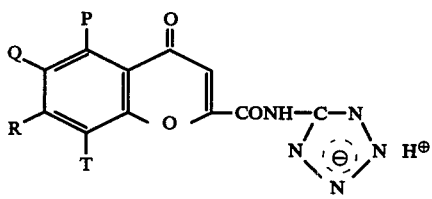

Ix in which one or more adjacent pairs of P, Q, R and T represent chain of formula XX or a group of formula X,

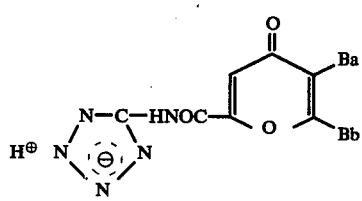

X in which Ba and Bb represent the pair of groups: a carbon-carbon bond and —CRa=CRb—; or an adjacent pair of P, Q, R and T represent a group of formula XI,

XI

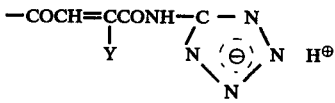

Ra and Rb and those of P, Q, R and T which do not form a chain of formula XX or a group of formula X or XI may be the same or different and each represents hydrogen; alkyl; alkoxy; alkenyl; alkenyloxy; alkyl or alkoxy, substituted by a hydroxy, alkoxy, aryl or halo group; amino; mono- or di-lower alkylamino; aminoalkoxy; aminoalkoxy substituted by a lower alkyl group; nitro; hydroxy; halogen; acyl; or aryloxy.

According to our invention we also provide a process for the production of a compound I, or a pharmaceutically acceptable derivative thereof, which comprises (a) removing a group $R_{11}$ from a compound (to be called a compound II) in which two chains of formula XXb,

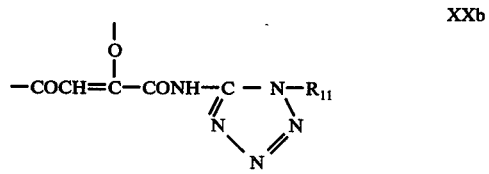

XXb in which $R_{11}$ represents a group which may be replaced by hydrogen, are attached to two pairs of ortho positions on a benzene or naphthalene nucleus, (b) removing both groups $R_{12}$ from a compound (to be called a compound VI) in which two chains of formula XXd,

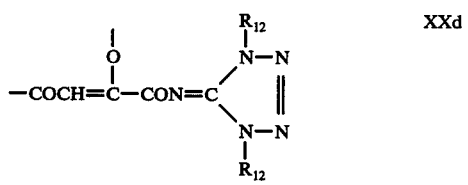

XXd in which $R_{12}$ represents a group which may be replaced by hydrogen, are attached to two pairs of ortho positions on a benzene or naphthalene nucleus, (c) cyclising a compound (to be called a compound VIII) in which two chains of formula XXe,

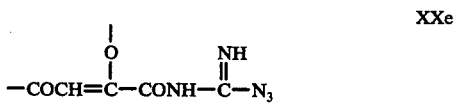

XXe are attached to two pairs of ortho positions on a benzene or naphthalene nucleus, (d) reacting a compound (to be called a compound III) in which two chains —COCH=C(COOH)—O— are attached to two pairs of ortho positions on a benzene or naphthalene nucleus, or an acid halide, an ester or a mixed anhydride thereof, with 5-aminotetrazole, (e) cyclising a compound (to be called a compound XII) in which two pairs of groups —OH and, —COCH=CCONH—C — N
       |       / \
       Y      N   N   H⊕
              \⊖/
               N in which Y is an —OH group or a group —NL₁L₂ in which $L_1$ and $L_2$, which are the same or different are each hydrogen, phenyl, lower alkyl, or together form a saturated or unsaturated 4 or 5 membered alkylene chain, are attached to two pairs of ortho positions on a benzene or naphthalene nucleus, or (f) selective dehydrogenation of a compound (to be called a compound XIII) in which two chains of formula XXf,

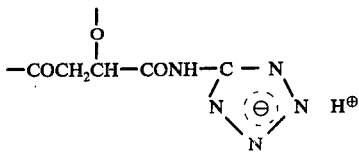  XXf are attached to two pairs of ortho positions on a benzene or naphthalene nucleus, and where desired or necessary converting the compound I to a pharmaceutically acceptable derivative thereof, or vice versa.

According to a preferred feature of our invention we provide a process for the production of a compound of formula Ix, or a pharmaceutically acceptable derivative thereof, which comprises (a) producing a compound of formula Ix by removing an $R_{11}$ group from a corresponding compound having an $R_{11}$ group on the 1-position of each carboxamido tetrazole group, (b) removing both $R_{12}$ groups from a corresponding compound in which the two carboxamido tetrazole groups are replaced by groups of formula,

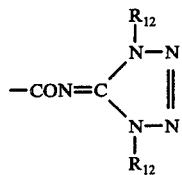

in which $R_{12}$ is as defined above, (c) cyclising a corresponding compound in which the two carboxamido tetrazole groups are replaced by groups of formula,

(d) reacting a corresponding compound in which the carboxamido tetrazole groups are replaced by —COOH groups (or an acid halide, ester or mixed anhydride thereof), with 5-aminotetrazole, (e) cyclising a compound of formula XII,

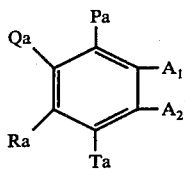  XII in which one or more adjacent pairs of Pa, Qa, Ra and Ta may represent the pair of groups $A_1$, $A_2$ or may represent a group of formula Xa,

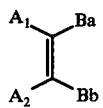

in which Ba and Bb are as defined above, or an adjacent pair of Pa, Qa, Ra and Ta form a group of formula XIa,

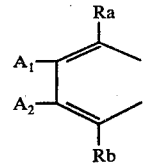  XIa

Ra, Rb and those of Pa, Qa, Ra and Ta which do not represent groups $A_1$ or $A_2$ or a group of formula Xa and XIa have the same significances as those of P, Q, R and T above which do not form a chain of formula XX or a group of formula X or XI, and $A_1$ and $A_2$ represent the groups —OH and,

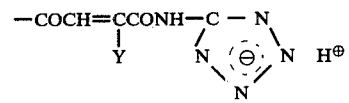

in which Y is as defined above, or (e) selective dehydrogenation of the corresponding tetrahydrodipyran, and when desired or necessary converting the compound of formula Ix to a pharmaceutically acceptable derivative thereof, or vice versa.

In process (a) the group $R_{11}$ may be, for example, an aralkyl, e.g. a benzyl, p-methoxybenzyl, triphenylmethyl or diphenylmethyl group; an aroylalkyl, e.g. a phenacyl group; an acyl, e.g. acetyl group; an amino group; or a group —$(CH_2)_2$G, where G is an electron withdrawing group, for example a nitrile, a carboxylic ester, e.g. of a lower alkanol, or an acyl group, e.g. an acetyl group.

When $R_{11}$ represents an aralkyl group the group may be removed either using a hydrogen halide, e.g. HBr, in acetic acid or by catalytic hydrogenation using, for example, a palladium catalyst in a solvent which is inert under the reaction conditions, e.g. acetic acid, or by using sodium in liquid ammonia.

When $R_{11}$ represents an acyl group, the group may be removed under basic conditions with, for example, sodium hydroxide.

When $R_{11}$ represents a group —$CH_2CH_2$G the group may be removed under basic conditions with, for example, sodium hydroxide.

When $R_{11}$ represents an amino group, the group may be removed by reductive de-amination with, for example, hypophosphorous acid, stannous chloride or sodium in liquid ammonia.

Process (b) may be carried out under the same conditions as specified above for process (a). $R_{12}$ may be a group $R_{11}$ as described above.

Process (c) may be carried out under basic conditions, e.g. by treating the compound VIII with a mild base such as sodium bicarbonate. Alternatively the cyclisation may be effected at an elevated temperature, for example of from 50° to 150° C, preferably in a solvent which is inert under the reaction conditions, e.g. dimethylformamide.

In process (d) the anhydride is preferably a mixed anhydride of such a type that it will cleave preferentially, to give the desired benzodipyran- or naphthodipyran-carboxamidotetrazole, as the major product when reacted with 5-aminotetrazole. Examples of suitable acids from which the mixed anhydride may be derived are sulphonic acids e.g. benzene sulphonic acid, sterically hindered carboxylic acids, e.g. pivalic, isovaleric, diethylacetic or triphenylacetic acid, and alkoxy formic acids, e.g. a lower alkoxy formic acid such as ethoxy or isobutoxy formic acid. When an acid halide is used it may conveniently be an acid chloride. The reaction is preferably carried out under anhydrous conditions in a solvent which will not react with either the 5-aminotetrazole or the mixed anhydride or acid halide, e.g. pyridine or dimethylformamide. However when the reaction is carried out in a non-basic solvent, e.g. dimethylformamide, an adequate proportion of an acid acceptor, e.g. triethylamine, should also preferably be present. The reaction is preferably carried out at a temperature of from about −15° to +20° C. When an ester is used we prefer to use a lower alkoxy ester and to carry out the reaction in a solvent which is inert under the reaction conditions, e.g. glacial acetic acid, at a temperature of from about 100° to 200° C. When a compound III itself is used the reaction may be carried out by heating the compound III and the 5-aminotetrazole in a solvent which is inert under the reaction conditions, e.g. dimethylacetamide, at a temperature of from 100° to 200° C. Alternatively the reaction may be carried out in the present of a condensation agent, e.g. N,N′-carbonyldiimidazole or dicyclohexyl carbodiimide, in an aprotic solvent, e.g. dimethylformamide, at a temperature of from about 10° to 40° C.

In process (c) the cyclisation may be carried out by heating or under basic or neutral conditions. It is, however, preferred to carry out the cyclisation in the presence of an acid, e.g. hydrochloric acid, and in a solvent which is inert under the reaction conditions, e.g. ethanol or dimethylacetamide. The reaction may be carried out at a temperature of from 20° to 150° C.

In process (f) the dehydrogenation may be carried out using a mild oxidising agent, e.g. selenium dioxide or chloranil. Alternatively the dehydrogenation may be carried out indirectly by halogenation followed by dehydrohalogenation, for example by treatment with N-bromosuccinimide or pyridinium bromide perbromide to yield the 3-bromo derivative, which is subsequently dehydrobrominated. The reaction may be carried out in a solvent which is inert under the reaction conditions, e.g. a halogenated hydrocarbon such as chloroform, xylene or glacial acetic acid. The reaction may be carried out at a temperature of from about 20° to 150° C.

The compounds I may be recovered from the reaction mixture using conventional techniques.

The compounds II may be made by reaction of a compound III, or an acid halide, ester or a mixed anhydride thereof with a compound of formula V,

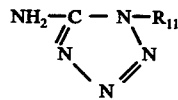

in which $R_{11}$ is as defined above. The reaction may be carried out under the conditions set out for process (d) above.

The acid halides, esters and the mixed anhydrides of the compounds III, the compounds III themselves, and the compounds of formula V are either known or may be made by methods known for the manufacture of similar known compounds.

The compounds VI may be made by reacting a compound (to be called a compound VII), in which two chains of formula XXg,

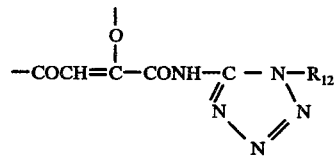

in which $R_{12}$ is as defined above, are attached to two pairs of ortho positions on a benzene or naphthalene nucleus, with a compound $R_{12}Hal$ in which Hal represents a halogen atom and $R_{12}$ is as defined above. The reaction may be carried out by reacting the compound VII with sodium hydride in hexamethylphosphoramide as solvent, and then adding the compound $R_{12}Hal$, e.g. benzyl bromide with stirring at room temperature.

The compounds VII may be made from compounds III by processes analogous to process (d) above.

The compounds VIII may be made by reacting an acid halide of a compound III with 5-aminotetrazole. The reaction may be carried out in a suitable solvent which is inert under the reaction conditions and in the presence of an acid acceptor, e.g. triethylamine in dimethylacetamide. Alternatively the reaction may be carried out in a basic solvent, e.g. pyridine. The compounds VIII are interemediates in process (d) above.

Compounds XII in which Y is —OH may be made by reacting a compound (to be called a compound XIV) in which two pairs of groups —OH and —COCH$_3$ are attached to two pairs of ortho positions on a benzene or naphthalene nucleus, with a compound of formula XV,

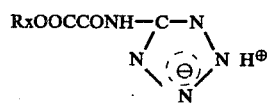

in which Rx is an alkyl Cl to 6 groups. The reaction may be carried out under conditions conventional for a Claisen condensation.

Compounds XII in which Y is an —OH group may also be prepared by the action of mild alkali on a compound I. Compounds XII in which Y is a group —NL$_1$L$_2$ may be made by the action of an amine HNL$_1$L$_2$ on a compound I.

Compounds XIII may be made by selective hydrogenation of a compound I or by a method analogous to process (d) above using a compound (to be called a compound XVI) in which two chains —COCH$_2$CH(COOH)—O— are attached to two pairs of ortho positions on a benzene or naphthalene nucleus, or an acid halide, an ester or a mixed anhydride thereof.

Compounds XIV and XVI and compounds of formula XV are either known or may be made from known compounds using techniques known per se.

Some of the groups P, Q, R, T, R$a$ or R$b$ may be affected by the reaction conditions described above. Where necessary or desirable therefore the reaction may be carried out using protected derivatives of the reagents.

The processes described above may, of course, be used to prepare compounds of formula Ix. The processes described above may produce the compound I or a derivative thereof. It is also within the scope of this invention to treat any derivative so produced to liberate the free compound I, or to convert one derivative into another. Suitable derivatives include salts and notably water-soluble salts. Salts which may be mentioned include salts with inorganic alkalis, such as the alkali-metal and alkaline-earth metal salts e.g. the potassium, lithium and calcium salts and, notably the sodium salt. Other salts include salts with organic bases, e.g. bases containing both nitrogen and oxygen atoms. Specifically there may be mentioned salts with alkanolamines, e.g. tri- and di-ethanolamine; hydroxyalkylalkylamines, e.g. tri-(hydroxymethyl) methylamine; 5 or 6 membered nitrogen containing heterocyclic rings, e.g. morpholine; and N-alkylamino substituted sugars, e.g. N-methyl-glucamine.

According to our invention we also provide a process for the production of a pharmaceutically acceptable salt of a compound I which comprises treating a compound I or a salt thereof, with a compound containing an available pharmaceutically acceptable cation, e.g. a base, or with an appropriate salt using a metathetical process.

The compounds I, and pharmaceutically acceptable derivatives thereof, are useful because they possess pharmacological activity in animals; in particular they are useful because they inhibit the release and/or action of pharmacological mediators which result from the in vivo combination of certain types of antibody and specific antigen, e.g. the combinations of reaginic antibody with specific antigen. (See Example A below).

In man, both subjective and objective changes which result from the inhalation of specific antigen by sensitised subjects are inhibited by prior administration of the new compounds. Thus the new compounds are useful in the treatment of asthma, e.g. allergic asthma. The new compounds are also useful in the treatment of so-called 'intrinsic' asthma (in which no sensitivity to extrinsic antigen can be demonstrated). The new compounds are also useful in the treatment of other conditions in which antigen-antibody reactions are responsible for disease, for example, hay fever; certain eye conditions, e.g. trachoma; urticaria; and gastrointestinal allergy, especially in children, e.g. milk allergy.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example A. For man the total daily dosage is in the range of from about 1 mg to 3,500 mg which may be administered in divided doses from 1 to 6 times a day or in sustained release form. Thus dosage forms suitable for administration (by inhalation or oesophageally) comprise from about 0.17 mg to 600 mg of the compound admixed with a solid or liquid pharmaceutically acceptable diluent or carrier.

According to our invention we also provide a pharmaceutical composition comprising (preferably a minor proportion of) a compound I, or a pharmaceutically acceptable derivative thereof, in combination with a pharmaceutically acceptable adjuvant, diluent or carrier. Examples of suitable adjuvants, diluents or carriers are: for tablets and dragees; lactose, starch, talc or stearic acid; for capsules; tartaric acid or lactose; for suppositories and ointments, natural or hardened oils or waxes; for inhalation compositions, coarse lactose. For use in inhalation (and other) compositions the compounds I, or the pharmaceutically acceptable derivative thereof, preferably has a fine particle size of from 0.01 to 10 microns and may if desired be used in combination with a bronchodilator, e.g. isoprenaline. The compound of fine particle size may be made, for example by grinding or milling. The compositions may also contain suitable preserving, stabilising and wetting agents, solubilisers, sweetening and colouring agents and flavourings. The compositions may, if desired, be formulated in sustained release form. Compositions for inhalation may also comprise a solution, e.g. an aqueous solution, of the compound I or the pharmaceutically acceptable derivative thereof; or may comprise a mixture of the compound with a liquifyable gas, under pressure, the mixture being put up in a container having a valve adapted to dispense a metered dose.

R$a$, R$b$ and those of P, Q, R and T which do not form a chain of formula XX or a group of formula X or XI preferably each contain 10 or less carbon atoms, and are preferably hydrogen; lower alkyl; lower alkoxy; lower alkenyl; lower alkenyloxy; lower alkyl or lower alkoxy substituted by hydroxy, phenyl, lower alkoxy or chlorine; amino; mono- or di-lower alkyl amino; amino lower alkoxy; nitro; hydroxy; chlorine; bromine; or lower acyl.

As a specific group of compounds of formula I$x$ we provide those compounds in which no adjacent pairs of P, Q, R and T represent a group of formula X or XI. More specifically we provide compounds of formulae I$n$, I$o$ and I$p$,

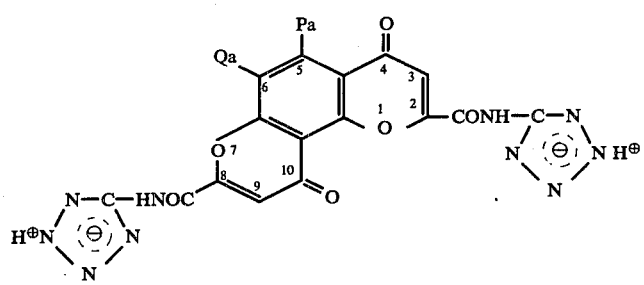

In

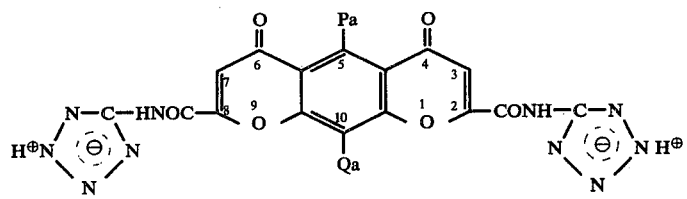

Io

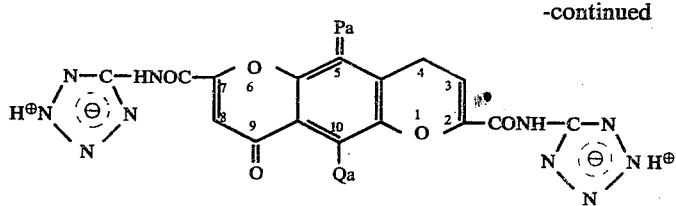

in which formulae Pa and Qa have the same significances as P, Q, R and T above, save that Pa and Qa do not together form a group of formula X or a chain of formula XX.

In this specification and in the claims the term 'lower' is used to indicate that the group contains from 1 to 6 carbon atoms.

The invention is illustrated, but in no way limited by the following Examples.

EXAMPLE 1

5-Methoxy-4,10-dioxo-4H,10H-benzo[1,2-b:3,4-b']dipyran-2,8-di-[N-(tetrazol-5-yl)]carboxamide (a) 5-Methoxy-4,10-dioxo-4H,10H-benzo[1,2-b:3,4-b']dipyran-2,8-dicarbonyl chloride 5-Methoxy-4,10-dioxo-4H,10H-benzo[1,2-b:3,4-b']dipyran-2,8-dicarboxylic acid (28.0 gm) and thionyl chloride (22.4 gm) were heated at reflux in dichloroethane (800 ml) containing dimethylformamide (16 drops) for 16 hours. The mixture was cooled and filtered giving white needles of the di-acid chloride, 25.0 gm., m.p. 242°-3° C (d).

Analysis: found: C, 48.9; H, 1.65%; $C_{15}H_6Cl_2O_7$ requires. C, 48.8; H, 1.6%.

SPECTRAL CONFIRMATION

The molecular weight was shown to be 368 by mass spectrometry. The i.r. spectrum displayed carbonyl bands at 1760 $cm^{-1}$ and 1650 $cm^{-1}$ due to the acid chloride and 4-oxo groups respectively. The n.m.r. spectrum in deuterochloroform showed three singlets at 2.8τ ($H_3$ and $H_9$), 3.1τ ($H_6$) and 5.93τ ($OCH_3$). Further confirmation of the structure of the acid chloride was obtained by preparation and characterisation of the bis anilide.

(b) 5-Methoxy-4,10-dioxo-4H,10H-benzo[1,2-b:3,4-b']dipyran-2,8-di-[N-(tetrazol-5-yl)]carboxamide To a stirred mixture of 5-methoxy-4,10-dioxo-4H,10H-benzo[1,2-b:3,4-b']dipyran-2,8-dicarbonyl chloride (24.0 gm.) and anhydrous 5-aminotetrazole (30.0 gm.) in dimethylacetamide (200 ml) was added triethylamine (40 ml.). Immediate solution occurred and the mixture was heated at 100° C for 1½ hours after which time precipitation was complete. The mixture was filtered and the residue was washed with hot dimethylacetamide and dried under vacuum at 80° C giving 5-methoxy-4,10-dioxo-4H,10H-benzo[1,2-b:3,4-b']dipyran-2,8-di-(tetrazol-5-yl)] carboxamide as a buff solid (11.0 gm) m.p. 300° C.

Analysis: Found C, 42.0; H, 2.8; N, 29.0%; $C_{17}H_{10}N_{10}O_7$ with 4.1% water requires: C, 42.0; H, 2.6; N, 28.8%.

SPECTRAL CONFIRMATION

The i.r. spectrum showed —NH bands from 3500 - 3260 $cm^{-1}$, amide carbonyl bands at 1720 and 1705 $cm^{-1}$ and a strong band at 1660 $cm^{-1}$ due to the 4-oxo groups. The n.m.r. spectrum in hexadeuterodimethyl sulphoxide revealed four singlet peaks at 2.95, 3.12, 3.22 and 6.05τ, that at highest field being due to the methoxyl group. The NH protons gave broad low field signals.

(c) 5-Methoxy-4,10-dioxo-4H,10H-benzo[1,2-b:3,4-b']dipyran-2,8-di-[N-(tetrazol-5-yl)]carboxamide, sodium salt Water (400 ml.) was added to an intimate mixture of 5-methoxy-4,10-dioxo-4H,10H-benzo[1,2-b:3,4-b']dipyran-2,8-di-[N-(tetrazol-5-yl)] carboxamide (10.25 gm.) and sodium bicarbonate (3.70 gm.). The solution obtained was cooled in ice and excess ethanol was added causing precipitation of the disodium salt. The solid was filtered and crystallised from a mixture of water and ethanol giving 5-methoxy-4,10-dioxo-4H,10H-benzo[1,2-b:3,4-b']dipyran-2,8-di[N-(tetrazol-5-yl)]carboxamide disodium salt trihydrate as a yellow solid, 10.0 gm.

Analysis: Found: C, 36.3; H, 2.5; N, 24.7%; $C_{17}H_8N_{10}Na_2O_7.3H_2O$ requires: C, 36.3; H, 2.45; N, 24.9%.

SPECTRAL CONFIRMATION

The i.r. spectrum showed a broad band at 1700 $cm^{-1}$ due to the amide carbonyls and a similar band at 1660 $cm^{-1}$ due to the 4-oxo carbonyls. The n.m.r. spectrum in hexadeuterodimethylsulphoxide showed four singlets at 2.65, 3.1, 3.22 and 6.05τ. That at highest field was due to the methoxyl group.

EXAMPLE 2

5-Methoxy-4,10-dioxo-4H,10H-benzo[1,2-b:3,4-b']dipyran-2,8di-[N-(tetrazol-5-yl)]carboxamide, di-triethanolamine salt.

A suspension of 5-methoxy-4,10-dioxo-4H,10H-benzo[1,2-b:3,4-b']dipyran-2,8-di-[N-(tetrazol-5-yl)]carboxamide (2.5 gm) in water (30 ml) was stirred while a solution of triethanolamine (1.60 gm) in water (20 ml) was added. The mixture was heated, to effect complete reaction, filtered and the filtrate was freeze-dried giving the required salt as a yellow powder (3.2 gm, 78%) mp 150°-2° C (d).

Analysis: Found: C, 44.58; H, 5.63; N, 21.68%; $C_{29}H_{40}N_{12}O_{13}$ requires with 2.11% water content C, 44.58; H, 5.4; N, 21.5%.

SPECTRAL CONFIRMATION

The infra-red spectrum showed bands due to the amide carbonyl at 1700 $cm^{-1}$ and the pyrone carbonyl at 1650 $cm^{-1}$. The nmr spectrum in hexadeuterodimethylsulphoxide displayed singlets at 2.76, 3.07, 3.2 and 6.0τ in the ratio 1:1:1:3 and two triplets at 6.3 and 6.85τ due to the methylene groups of the triethanolamine residue.

EXAMPLE 3

5-Methoxy-4,10-dioxo-4H,10H-benzo[1,2-b:3,4-b']dipyran-2,8-di-[N-(tetrazol-5-yl)]carboxamide, di-(N-methylglucamine salt).

To a stirred suspension of 5-methoxy-4,10-dioxo-4H,10H-benzo[1,2-b:3,4-b']dipyran-2,8-di-[N-(tetrazol-5-yl)]-carboxamide (2.5 gm) in water (30 ml) was added a solution of N-methylglucamine (2.095 gm) in water (20 ml). The mixture was heated to effect complete reaction, and was then filtered. The filtrate was freeze-dried giving the required salt as a yellow powder (4.0 gm, 85%), mp 140°-2° C, (d).

Analysis: Found: C, 43.0; H, 5.3; N, 19.03%; $C_{31}H_{44}N_{12}O_{17}$ requires with 1% water content C, 43.0; H, 5.2; N, 19.4%.

SPECTRAL CONFIRMATION

The infra-red spectrum was very broad in the region 3200-2000 $cm^{-1}$ (NH and OH stretch). The amide carbonyls occurred at 1700 $cm^{-1}$ and the pyrone carbonyls at 1650 $cm^{-1}$. The nmr spectrum in hexadeuterodimethylsulphoxide displayed singlets at 2.6, 3.06, 3.2 and 6.0$\tau$ in the ratio 1:1:1:3. The multiplet at 6.3 – 7.4$\tau$ was due to the protons of the sugar residue.

EXAMPLE 4

5-Methoxy-4,10-dioxo-4H,10H-benzo[1,2-b:3,4-b']dipyran-2,8-di-[N-(tetrazol-5-yl)]carboxamide, calcium salt.

To an intimate mixture of 5-methoxy-4,10-dioxo-4H,10H-benzo [1,2-b:3,4-b']dipyran-2,8-di-[N-(tetrazol-5-yl)]carboxamide (10.0 gm) and sodium hydrogen carbonate (3.60 gm) was added water (200 ml). The mixture was heated and stirred until reaction was complete. The mixture was filtered.

A solution of calcium nitrate (3.52 gm) in water (10 ml) was added to the filtrate with stirring at room temperature. After the addition the mixture was cooled in ice and filtered. The solid so obtained was washed well with ethanol and dried in vacuo at 90° C giving the calcium salt as a yellow powder (10.4 gm), mp>250° C.

Analysis: Found: C, 32.2; H, 3.2; N, 22.5%; $C_{17}H_8CaN_{10}O_7$ requires with 20.4% water C, 32.2; H, 3.5; N, 22.5%.

SPECTRAL CONFIRMATION

The infra-red spectrum was consistent with the required structure having the amide carbonyl band at 1690 $cm^{-1}$. The nmr spectrum in hexadeuterodimethylsulphoxide showed four singlets at 2.7, 3.09, 3.11 and 6.0$\tau$ in the ratio 1:1:1:3.

EXAMPLE 5

5-Methoxy-4,10-dioxo-4H,10H-benzo[1,2-b:3,4-b']dipyran-2,8-di-[N-(tetrazol-5-yl)]carboxamide dilithium salt.

To a stirred suspension of 5-methoxy-4,10-dioxo-4H,10H-benzo [1,2-b:3,4-b']dipyran-2,8-di-[N-(tetrazol-5-yl)]carboxamide (1.00 gm) in water (40 ml) was added a solution of lithium hydroxide monohydrate (0.18 gm) in water (10 ml). The solution was filtered and freeze dried giving the dilithium salt as a yellow powder (0.95 gm), mp>250° C.

Analysis: Found: C, 37.4; H, 2.8; N, 25.5%; $C_{17}H_8Li_2N_{10}O_7$ requires with 12.2% water content C, 37.5; H, 2.85; N, 25.7%.

SPECTRAL CONFIRMATION

The nmr spectrum in hexadeuterodimethylsulphoxide displayed four singlets at 2.65, 3.05, 3.18 and 6.0$\tau$ in the ratio 1:1:1:3. The infra-red spectrum of the salt was consistent with the required structure having the amide carbonyl band at 1690 $cm^{-1}$, and other bands due to the 4-oxo groups and aromatic ring.

EXAMPLE 6

5-Methoxy-4,10-dioxo-4H,10H-benzo[1,2-b:3,4-b']dipyran-2,8-di-[N-(tetrazol-5-yl)]carboxamide dipotassium salt.

To an intimate mixture of 5-methoxy-4,10-dioxo-4H,10H-benzo[1,2-b:3,4-b']dipyran-2,8-di-[N-(tetrazol-5-yl)]carboxamide (7.00 gm) and potassium hydrogen carbonate (3.00 gm) was added water (350 ml) and the mixture was heated to effect solution. The solution was filtered and cooled. Addition of acetone gave the required dipotassium salt as a yellow solid (4.5 gm), mp>250° C.

Analysis: Found: C, 33.3; H, 2.6; N, 22.8%; $C_{17}H_8K_2N_{10}O_7$ requires with 11.5% water C, 33.3; H, 2.6; N, 22.85%.

SPECTRAL CONFIRMATION

The nmr spectrum in hexadeuterodimethylsulphoxide showed four singlets at 2.62, 3.08, 3.2 and 6.0$\tau$ in the ratio 1:1:1:3. The infra-red spectrum was very much broadened having the amide carbonyl band at 1690 $cm^{-1}$.

EXAMPLE 7

5Methoxy-4,10-dioxo-4H,10H-benzo[1,2-b:3,4-b']dipyran-2,8-di-[N-(tetrazol-5-yl)]carboxamide di-tris-(hydroxymethyl) methylamine salt.

Tris-(hydroxymethyl)methylamine (2.6 g; 0.02146 mole) and 5-methoxy-4,10-dioxo-4H,10H-benzo[1,2-b:3,4-b']dipyran-2,8-di-[N-(Tetrazol-5-yl)]carboxamide (5 g; 0.01073 mole) were heated in water (100 ml) until complete dissolution was obtained. The solution was filtered and the filtrate was freeze-dried to give the desired salt, which was dried in vacuo (7.0 g), mp 160°-175° decomp.

Analysis: Found: C, 39.9; H, 4.9; N, 22.05%; $C_{25}H_{32}N_{12}O_{13}$ requires with 5.8% water content C, 39.9; H, 4.9; N, 22.3%.

SPECTRAL CONFIRMATION

The infra-red spectrum displayed peaks at 1700 (amide I) $cm^{-1}$, 1650 (4-oxo) $cm^{-1}$ and 1600 $cm^{-1}$.

EXAMPLE 8

5-Methoxy-4,10-dioxo-4H,10H-benzo[1,2-b:3,4-b']dipyran-2,8-di-[N-(tetrazol-5yl)]carboxamide di-morpholine salt.

Morpholine (1.87 g; 0.02146 mole) was added to a suspension of 5-methoxy-4,10-dioxo-4H,10H-benzo[1,2-b:3,4-b']dipyran-2,8-di-[N-(tetrazol-5-yl)]carboxamide (5.0 g; 0.01073 mole) in water (50 ml). The mixture was heated until all the material had dissolved. The resulting solution was filtered and the filtrate was freeze dried. The desired salt so obtained was dried in vacuo at 70° C (5.9 g), mp 231° C decomp.

Analysis: Found: C, 44.0; H, 5.1; N, 24.4%; $C_{24}H_{28}N_{12}O_9 \cdot 4H_2O$ requires: C, 44.0; H, 5.0; N, 24.6%.

SPECTRAL CONFIRMATION

The infra-red spectrum displayed peaks at 1700 (amide I) $cm^{-1}$, 1650 (4-oxo) $cm^{-1}$ and 1600 (aromatic) $cm^{-1}$.

EXAMPLE 9

5-Methoxy-4,10-dioxo-4H,10H-benzo[1,2-b:3,4-b']dipyran-2,8-di-[N-(tetrazol-5-yl)]carboxamide diethanolamine salt.

Ethanolamine (1.2 ml; 0.0286 mole) was added to a suspension of 5-methoxy-4,10-dioxo-4H,10H-benzo[1,2-b:3,4-b']dipyran-2,8-di-[N-(tetrazol-5-yl)]carboxamide (5 g; 0.01073 mole) in water (75 ml). The mixture was heated until all the material had dissolved. The resulting solution was freeze dried. The desired salt so obtained was dried, washed with ether and re-dried in vacuo (5.2 g) mp 182° decomp.

Analysis: Found: C, 41.4; H, 4.7; N, 27.9%; $C_{21}H_{24}N_{12}O_9$ requires with 3.5% water content C, 41.3; H, 4.5; N, 27.5%.

SPECTRAL CONFIRMATION

The infra-red spectrum displayed peaks at 1700 (amide I) cm$^{-1}$, 1650 (4-oxo) cm$^{-1}$ and 1600 cm$^{-1}$.

EXAMPLE 10

5-Methoxy-4,10-dioxo-4H,10H-benzo[1,2-b:3,4-b']dipyran-2,8-di[N-(tetrazol-5-yl)]carboxamide.

A suspension of 3,5-dihydroxy-2,4-di(3-[N-(tetrazol-5-yl)carboxamido]-1,3-dioxopropyl)anisole (1.0 gm) in a solution of dimethylacetamide (10 ml), and concentrated hydrochloric acid (1 ml) was heated under gentle reflux for 1 hour. The mixture was filtered and the residue washed with hot dimethylacetamide and dried under vacuum at 80° C giving 5-methyl-4,10-dioxo-4H,10H-benzo[1,2-b:3,4-b']dipyran-2,8-di[N-(tetrazol-5yl)]carboxamide as a buff solid mp>300° C.

EXAMPLE 11

5-Methoxy-4,10-dioxo-4H,10H-benzo[1,2-b:3,4-b']dipyran-2,8-di[N-(tetrazol-5-yl)]carboxamide A mixture of 5-methoxy-4,10-dioxo-2,3,8,9-tetrahydro-4H,10H-benzo[1,2-b:3,4-b']dipyran-2,8-di[N-(tetrazol-5-yl)]carboxamide (0.1 gm), pyridinium bromide perbromide (0.2 gm) and glacial acetic acid (115 ml) was stirred at ambient temperature for 18 hours. The mixture was then evaporated in vacuo, and the residue was washed with water and dried giving 5-methoxy-4,10-dioxo-4H,10H-benzo-[1,2-b:3,4-b']dipyran-2,8-di[N-(tetrazol-5-yl)]carboxamide as a buff solid mp>300° C.

EXAMPLE 12

The following compounds may be made by the process of Example 1 using appropriate starting materials.
4,10-Dioxo-5-methoxy-4H,10H-benzo(1,2-b:3,4-b')dipyran-2,8-di-[N-(tetrazol-5-yl)]carboxamide.
4,10-Dioxo-5-hydroxy-4H,10H-benzo(1,2-b:3,4-b')dipyran-2,8-di-[N-(tetrazol-5-yl)]carboxamide.
4,10-Dioxo-5-methyl-4H,10H-benzo(1,2-b:3,4-b')dipyran-2,8-di-[N-(tetrazol-5-yl)]carboxamide.
4,10-Dioxo-4H,10H-benzo(1,2-b:3,4-b')dipyran-2,8-di-[N-(tetrazol-5-yl)]carboxamide.
4,6-Dioxo-10-nitro-4H,6H-benzo(1,2-b:5,4-b')dipyran-2,8-di-[N-(tetrazol-5-yl)]carboxamide.
6-Bromo-4,10-dioxo-5-hydroxy-4H,10H-benzo(1,2-b:3,4-b')dipyran-2,8-di-[N-(tetrazol-5-yl)]carboxamide.
4,6-Dioxo-4H,6H-benzo(1,2-b:5,4-b')dipyran-2,8-di-[N-(tetrazol-5-yl)]carboxamide.
5-Benzyloxy-4,10-dioxo-4H,10H-benzo(1,2-b:3,4-b')dipyran-2,8-di-[N-(tetrazol-5-yl)]carboxamide.
5Methoxy-4,6-dioxo-4H,6H-benzo(1,2-b:5,4-b')dipyran-2,8-di-[N-(tetrazol-5-yl)]carboxamide.
4,10-Dioxo-6-ethyl-4H,10H-benzo(1,2-b:3,4-b')dipyran-2,8-di-[N-(tetrazol-5-yl)]carboxamide.
4,6-Dioxo-10-ethyl-4H,6H-benzo(1,2-b:3,4-b')dipyran-2,8-di-[N-(tetrazol-5-yl)]carboxamide.
4,10-Dioxo-6-chloro-4H,10H-benzo(1,2-b:3,4-b')dipyran-2,8-di-[N-(tetrazol-5-yl)]carboxamide.
4,10-Dioxo-5-allyloxy-4H,10H-benzo(1,2-b:3,4-b')dipyran-2,8-di-[N-(tetrazol-5-yl)]carboxamide.
10-Butyl-4,6-dioxo-4H,6H-benzo(1,2-b:5,4-b')dipyran-2,8-di-[N-(tetrazol-5-yl)]carboxamide.
4,6-Dioxo-10-n-pentyl-4H,6H-benzo(1,2-b:5,4-b')dipyran-2,8-di-[N-(tetrazol-5-yl)]carboxamide.
5-Methoxy-4,6-dioxo-10-propyl-4H,6H-benzo(1,2-b:5,4-b')dipyran-2,8-di-[N-(tetrazol-5-yl)]carboxamide.
5-Methoxy-4,10-dioxo-6-propyl-4H,10H-benzo(1,2-b:3,4-b')dipyran-2,8-di-[N-(tetrazol-5-yl)]carboxamide.
10-Ethyl-5-methyl-4,6-dioxo-4H,6H-benzo(1,2-b:5,4-b')dipyran-2,8-di-[N-(tetrazol-5-yl)]carboxamide.
4,9-Dioxo-4H,9H-benzo(1,2-b:4,5-b')dipyran-2,7-di-[N-(tetrazol-5-yl)]carboxamide.
4,6-Dioxo-10-propyl-4H,6H-benzo(1,2-b:5,4-b')dipyran-2,8-di-[N-(tetrazol-5-yl)]carboxamide.
4,10-Dioxo-5-ethoxy-4H,10H-benzo(1,2-b:3,4-b')dipyran-2,8-di-[N-(tetrazol-5-yl)]carboxamide.
4,6-Dioxo-10-ethoxymethyl-4H,6H-benzo(1,2-b:5,4-b')dipyran-2,8-di-[N-(tetrazol-5-yl)]carboxamide.
10-Bromo-4,6-dioxo-4H,6H-benzo(1,2-b:5,4-b')dipyran-2,8-di-[N-(tetrazol-5-yl)]carboxamide.
6Allyl-4,10-dioxo-5-methoxy-4H,10H-benzo(1,2-b:3,4-b')dipyran-2,8-di-[N-(tetrazol-5-yl)]carboxamide.
4,6-Dioxo-10-methyl-4H,6H-benzo(1,2-b:5,4-b')dipyran-2,8-di-[N-(tetrazol-5-yl)]carboxamide.

EXAMPLE 13

5-Methoxy-4,10-dioxo-4H,10H-benzo(1,2-b:3,4-b')dipyran-2,8-di-(N-(tetrazol-5-yl))carboxamide.

To a solution of 5-methoxy-4,10-dioxo-4H,10H-benzo(1,2-b:3,4-b')dipyran-2,8-di(5-carbonylimino-1,4-dibenzyltetrazoline) (0.2 gm) in glacial acetic acid (30 ml) containing concentrated hydrochloric acid (5 drops) was added 5% palladium on carbon catalyst (0.1 gm). The mixture was hydrogenated at 60° with a starting pressure of 45 psi for 24 hours. The catalyst was removed by filtration and the solvent evaporated in vacuo. The residue was washed well with ether and dried giving the title compound as a buff solid, m.p.>300°.

EXAMPLE 14

5-Methoxy-4,10-dioxo-4H,10H-benzo(1,2-b:3,4-b')dipyran-2,8-di-(N-(tetrazol-5-yl))carboxamide.

A solution of 5-methoxy-4,10-dioxo-4H,10H-benzo(1,2-b:3,4-b')dipyran-2,8-di(N-guanylazido)carboxamide (0.6 gm) in saturated aqueous sodium bicarbonate (10 ml) was heated at 100° for one hour. After cooling the solution was acidified with dilute hydrochloric acid. The resulting precipitate was removed by filtration, washed well with water and dried giving the title compound as a buff solid, m.p.>300°.

EXAMPLE A

The procedure set out below may be used to assess the effectiveness of a compound in inhibiting the release of the pharmacological mediators of anaphylaxis.

In this test, the effectiveness of the compounds in inhibiting the passive cutaneous anaphylactic reaction in rats is assessed. It has been proven that this form of test gives reliable qualitative indications of the ability of the compounds under test to inhibit antibody-antigen reactions in man.

In this test method Charles River France/Fisons bred rats (male or female) having a body weight of from 100 to 150 gms are infected subcutaneously at weekly intervals with *N. brasiliensis* larvae in doses increasing from about 2000 larvae per animal to 12000 larvae per animal in order to establish the infection. After 8 weeks the rats are bled by heart puncture and 15-20 mls. of blood collected from each animal. The blood samples are then centrifuged at 3500 rpm. for 30 minutes in order to remove the blood cells from the blood plasma. The serum is collected and used to provide a serum containing *N. brasiliensis* antibody. A pilot sensitivity test is carried out to determine the least quantity of serum required to give a skin weal in control animals in the test described below of 2 cm diameter. It has been found that optimum sensitivity of rats in the body weight range 100-130 gms is obtained using a serum diluted with eight parts of physiological saline solution. This diluted solution is called antibody serum A.

The antigen to react with the antibody in serum A is prepared by removing *N. brasiliensis* worms from the gut of the infested rats, centrifuging the homogenate and collecting the supernatent liquor. This liquor is diluted with saline to give a protein content of 1 mg/ml and is known as solution B.

Charles River France/Fisons bred rats in the body weight range 100 to 130 gms are sensitised by intradermal injection of 0.1 mls of serum A into the right flank. Sensitivity is allowed to develop for 24 hours and the rats are then injected intravenously with 1 ml/100 gms body weight of a mixture of solution B (0.25 mls), Evans Blue dye solution (0.25 mls) and the solution of the compound under test (0.5 mls varying percentages of active matter). Insoluble compounds are administered as a separate intraperitoneal injection 5 minutes before intravenous administration of solution B and Evans Blue dye. For each percentage level of active matter in the solution under test five rats are injected. Five rats are used as controls in each test. The dosages of the compound under test are selected so as to give a range of inhibition values.

Thirty minutes after injection of solution B the rats are killed and the skins removed and reversed. The intensity of the anaphylactic reaction is accessed by comparing the size of the characteristic blue weal produced by spread of the Evans Blue dye from the sensitisation site, with the size of the weal in the control animals. The size of the weal is rated as 0 (no weal detected, i.e. 100% inhibition) to 4 (no difference in size of weal, i.e. no inhibition) and the percentage inhibition for each dose level calculated as:

$$\% \text{ inhibition} = \frac{(\text{control group score} - \text{treated group score}) \times 100}{\text{Control group score}}$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal and gastric administration of the compound.

We claim:

1. The compound 4,10-dioxo-5-methoxy-4H,10H-benzo(1,2-b:3,4-b')dipyran-2,8-di[N-(tetrazol-5-yl)]carboxamide and pharmaceutically acceptable salts thereof.

2. The compound according to claim 1 which is 4,10-dioxo-5-methoxy-4H,10H-benzo(1,2-b:3,4-b')dipyran-2,8-di[N-(tetrazol-5-yl)]carboxamide.

3. The compound according to claim 1 which is 4,10-dioxo-5-methoxy-4H,10H-benzo(1,2-b:3,4-b')dipyran-2,8-di[N-(tetrazol-5-yl)]carboxamide disodium salt.

* * * * *